(12) United States Patent
Ohshima et al.

(10) Patent No.: US 7,426,023 B2
(45) Date of Patent: Sep. 16, 2008

(54) METHOD AND APPARATUS FOR DETECTING DEFECTS

(75) Inventors: Yoshimasa Ohshima, Yokohama (JP); Hisafumi Iwata, Hayama (JP); Hiroyuki Nakano, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 124 days.

(21) Appl. No.: 11/296,290

(22) Filed: Dec. 8, 2005

(65) Prior Publication Data

US 2006/0139629 A1    Jun. 29, 2006

(30) Foreign Application Priority Data

Dec. 9, 2004    (JP) .............................. 2004-356415

(51) Int. Cl.
   *G01N 21/00*    (2006.01)
(52) U.S. Cl. ............... 356/237.2; 356/237.1; 356/237.5
(58) Field of Classification Search ... 356/237.1–237.6; 250/559.01, 559.04, 550, 572
   See application file for complete search history.

(56) References Cited

U.S. PATENT DOCUMENTS

| | | | |
|---|---|---|---|
| 4,601,576 A | 7/1986 | Galbraith | |
| 5,172,000 A * | 12/1992 | Scheff et al. | 250/550 |
| 5,680,207 A * | 10/1997 | Hagiwara | 356/237.3 |
| 5,798,829 A | 8/1998 | Vaez-Iravani | |
| 5,903,342 A * | 5/1999 | Yatsugake et al. | 356/237.4 |
| 6,295,168 B1 | 9/2001 | Hoffnagle et al. | |
| 6,657,736 B1 * | 12/2003 | Finarov et al. | 356/625 |
| 6,798,584 B2 * | 9/2004 | Matsumoto et al. | 359/738 |
| 6,995,920 B2 * | 2/2006 | Nurishi | 359/668 |
| 7,187,438 B2 * | 3/2007 | Hamamatsu et al. | 356/237.4 |
| 7,248,354 B2 * | 7/2007 | Kreh et al. | 356/237.5 |

* cited by examiner

*Primary Examiner*—Sang Nguyen
(74) *Attorney, Agent, or Firm*—Antonelli, Terry, Stout & Kraus, LLP.

(57) ABSTRACT

There is disclosed a defect detecting apparatus that focuses a laser beam, irradiates it onto the surface of a sample to be examined, and detects a foreign substance/defect existing on the surface from the scattered light as a result of the irradiation of the beam onto the sample surface. In order to stably detect defects such as foreign substance, the defect detecting apparatus according to the invention is constructed to use a beam shape optical system by which the laser beam emitted from a laser source is shaped to change the illumination intensity from its Gauss distribution to a flat distribution so that the detected signal can be stably produced even if the relative position of a defect/foreign substance to the laser beam irradiation position is changed.

15 Claims, 9 Drawing Sheets

FIG.11
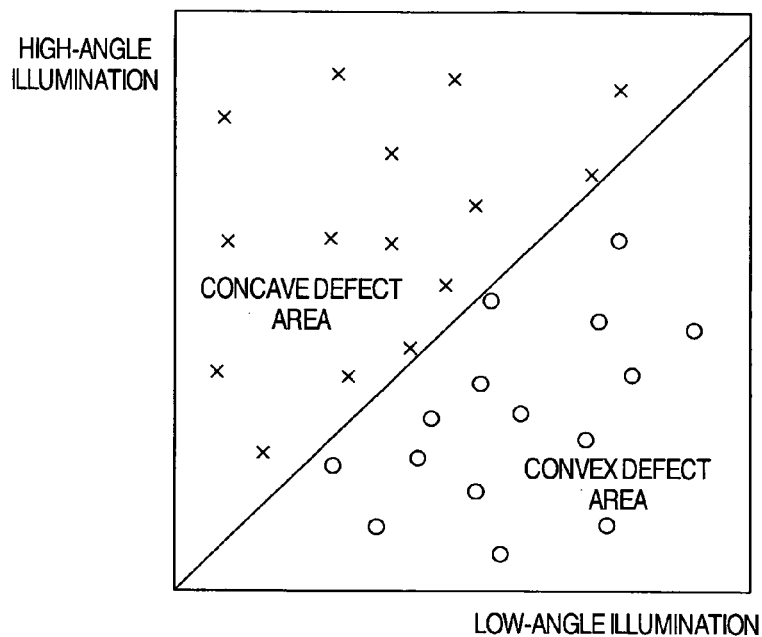
FIG.12A  FIG.12B
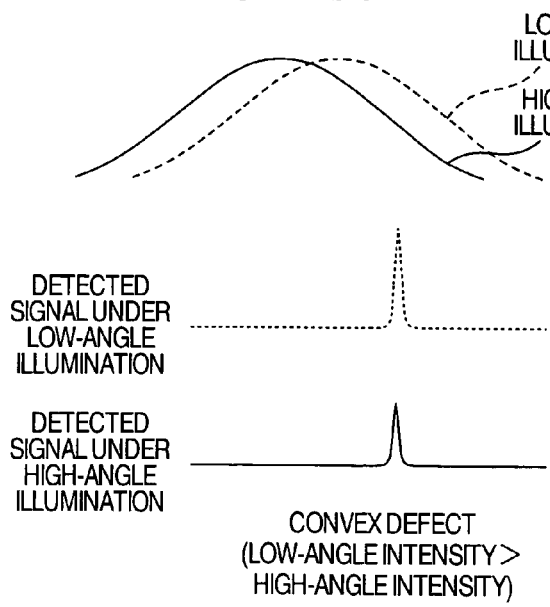
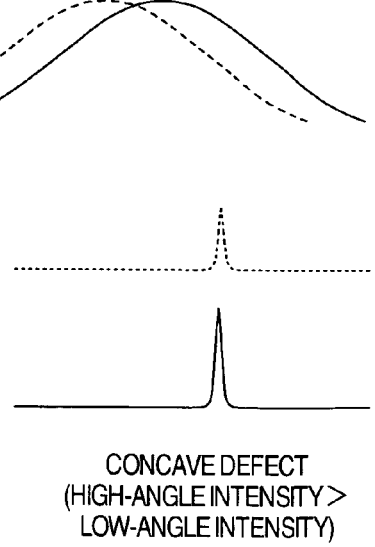

METHOD AND APPARATUS FOR DETECTING DEFECTS

INCORPORATION BY REFERENCE

The present application claims priority from Japanese application JP2004-356415 filed on Dec. 9, 2004, the content of which is hereby incorporated by reference into this application.

BACKGROUND OF THE INVENTION

The present invention relates to a defect detecting apparatus for sensitively and fast detecting minute extraneous substance or defects existing on semiconductor substrates.

The production lines for semiconductor substrates or thin film substrates examine for the foreign matter deposited on the surfaces of semiconductor substrates or thin film substrates in order to observe the dust-covered condition of the manufacturing apparatus. For example, any semiconductor substrate with circuit patterns not formed yet is subject to the test of if a minute foreign substance or defect of 0.1 μm or below is detected on its surface. There are prior arts for detecting very little defects on samples of semiconductor substrates as disclosed in U.S. Pat. No. 4,601,576 and U.S. Pat. No. 5,798,829. In these documents, a laser beam collected, or focused to a few tens of micrometers μm is irradiated on the sample surface, detects the scattered light from the foreign matter adhered or defect on the semiconductor substrate, and tests if there is a foreign substance or defect over the entire sample surface by rotating the sample and feeding it straight.

Since the irradiated laser beam usually has a Gauss distribution 201 as shown in FIG. 16, the beam irradiation density depends on the relative position of the existing foreign matter/defect to the irradiation position. That is, the scattered light intensity from even the same foreign substance/defect varies as indicated by detected signals 202, 203 and 204. The precision with which the test sample is placed and set on the sample stage is within the range from a few tens of μm to several hundreds of μm. The size, or diameter of the laser beam is similarly in the range from a few tens of μm to several hundreds of μm. Therefore, the relative position of the defect/foreign matter to the beam irradiation position changes each time the test is made, and thus the detected signal from the same foreign matter/defect varies. Accordingly, the reproducibility of the test is reduced. In addition, there is another prior art of U.S. Pat. No. 6,295,168 in which a construction for the test is disclosed.

The defect detecting apparatus for detecting the foreign matter/defect from the scattered light from the sample surface by focusing/irradiating a laser beam on the surface of the test sample can be adapted to prevent the reproducibility from lowering due to the Gauss distribution of the laser beam and to stably detect the foreign matter/defect.

SUMMARY OF THE INVENTION

According to the invention, there is provided a defect detecting apparatus constructed so that defects such as foreign substance can be stably examined.

That is, according to the invention, there is provided a defect detecting apparatus that shapes a laser beam to change the illumination intensity from its Gauss distribution to a flat distribution so that the detected signal can be stably produced even if the relative position of a defect/foreign substance to the laser beam irradiation position is changed.

In addition, according to the invention, there is provided a defect detecting apparatus that has a laser beam illumination optical system including a laser source for emitting a laser beam having a Gauss distribution in its illumination intensity, a beam shape optical system for shaping the laser beam from the laser source to have a flat distribution in its illumination intensity and a beam focusing optical system for focusing the shaped laser beam and irradiating the focused beam onto a substrate to be examined, a detection optical system for focusing the light scattered from the substrate as a result of the irradiation of the beam onto the substrate, receiving the focused scattered light and converting it into a signal, and a signal processor for detecting defects on the substrate on the basis of the signal produced by the conversion in the detection optical system.

The beam shape optical system in this invention is a diffraction optical element (DOE). In addition, the beam shape optical system in this invention is a homogenizer. Moreover, the laser beam illumination optical system further includes a beam expander provided between the beam shape optical system and the laser source so as to expand the beam diameter.

In addition, the laser beam illumination optical system in this invention is constructed to make high-angle illumination and low-angle illumination to the substrate by switching. Moreover, the signal processor in this invention is constructed so that a minute foreign substance and a minute concavo-convex defect existing on the substrate can be separately detected. Furthermore, the detection optical system in this invention is composed of a Fourier transform lens, an inverse Fourier transform lens and a spatial filter disposed in an image surface common to those Fourier transform lenses.

According to the invention, since the distribution-flattened laser beam is irradiated onto the substrate, the minute foreign substance/defects can be detected with stable sensitivity.

These and other objects, features and advantages of the invention will be apparent from the following more particular description of preferred embodiments of the invention, as illustrated in the accompanying drawings.

BRIEF DESCRIPTION OF THE DRAWINGS

FIG. 11 is a diagram useful for explaining that the convex-type defect and concave-type defect can be separately detected by irradiating at different angles and taking the ratio of scattered light intensities in the second embodiment of the invention.

FIG. 12A is a diagram showing detected signals obtained from the convex-type defect by low-angle illumination and high-angle illumination when the illumination beam has a Gauss distribution.

FIG. 12B is a diagram showing detected signals obtained from the concave-type defect by low-angle illumination and high-angle illumination when the illumination beam has a Gauss distribution.

DESCRIPTION OF THE EMBODIMENTS

Embodiments of the defect detecting apparatus according to the invention will be described with reference to the drawings.

The first embodiment of the defect detecting apparatus for detecting foreign substance and defects on a semiconductor wafer according to the invention will be first described with reference to FIGS. 1 through 5.

Figure 1A:
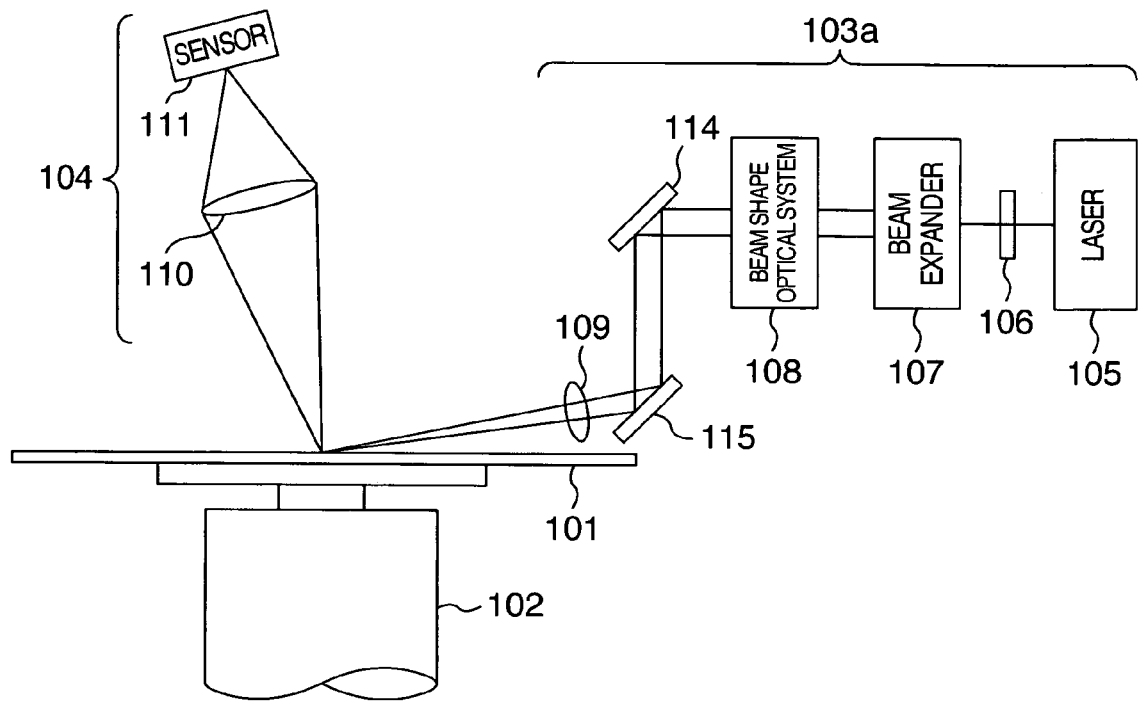
FIG. 1A is a diagram showing a first embodiment of a defect detecting apparatus for detecting foreign substance and defects on a semiconductor wafer according to the invention.

FIG. 1A is a diagram showing the first embodiment of the apparatus for detecting foreign substance and defects on the semiconductor wafer according to the invention. The defect detecting apparatus has an illumination optical system 103a for oblique illumination (dark-field illumination) to the detection area on a semiconductor wafer (inspected substrate) 101 placed on a wafer stage 102, and a detection optical system 104 for focusing and detecting the scattered light from the detection area on the semiconductor wafer 101 so as to convert it to a signal. The illumination optical system 103a includes a laser source 105 such as Ar (argon) laser or semiconductor laser, a ½, ¼ wavelength plate for adjusting the polarity direction of linear polarized light, a beam expander 107 for expanding the beam diameter, a beam shape optical system 108 for uniformly shaping the illumination intensity distribution of the laser beam, and a condenser 109.

The laser beam emitted from the laser source 105 is arbitrarily adjusted in its polarization direction by the wavelength plate 106. Then, it is expanded in its diameter by the beam expander 107, and focused and irradiated by the condenser 109 so that the semiconductor wafer 101 can be illuminated at the detection area by the focused beam. Shown at 114 and 115 are mirrors, which are used, as circumstances demand, to change the light paths for illumination. The beam shape optical system 108 shapes the illumination intensity distribution of the laser beam to change to a flat shape from the Gauss distribution.

Figure 1B:
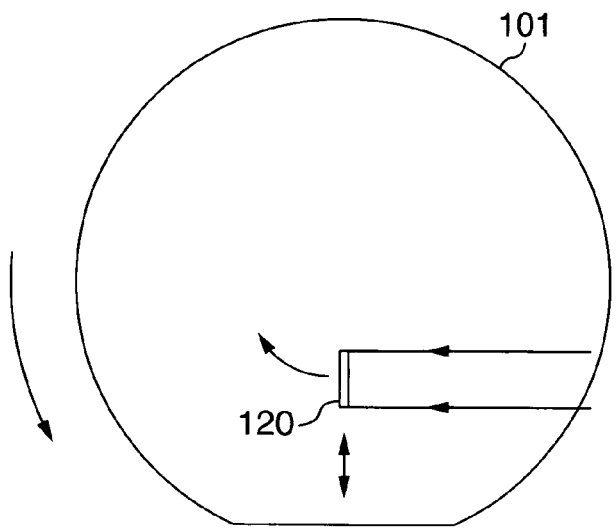
FIG. 1B is a diagram useful for explaining a slit-shaped beam that is irradiated to scan at an angle to the detection area.

The detection optical system 104 includes a scattered light detection lens 110 and a photoelectric transducer 111. The scattered light from a foreign substance and defect existing at the detection area is focused by the scattered light detection lens 110 so as to substantially hit the acceptance surface of the photoelectric transducer 111. The detection optical system 104 also includes the optical process for the scattered light from the foreign substance and defect, for example, the change/adjustment of the optical characteristics by a polarization plate or spatial filter. The photoelectric transducer 111 generates an electric signal of which the intensity is proportional to the amount of scattered light. This signal is processed by a signal processor (not shown) so that the foreign substance and defect can be detected and that their sizes can be measured. The photoelectric transducer 111 is used to receive the scattered light focused by the detection optical system 104 and to convert it to the electric signal. This transducer 111 may be, for example, a TV camera, CCD linear sensor, TDI (time delay integration) sensor or photoelectron multiplier. When a slit-shaped beam 120 is irradiated to the detection area in the oblique direction as illustrated in FIG. 1B, a CCD linear sensor or TDI sensor is desirable as the photoelectric transducer 111.

The wafer stage 102 is comprised of a chuck (not shown) to hold the wafer 101, a rotation mechanism (not shown) to rotate the wafer 101 and a straight feed mechanism (not shown) to straight feed the wafer 101 in the radius direction. Therefore, the wafer stage 102 horizontally rotates the wafer 101 and moves it straight as indicated by the arrows in FIG. 1B so that the waver 101 can be scanned, for example, spirally by the slit-shaped beam 120. As a result, it is possible to detect the foreign substances and defects and to measure the sizes thereof over the entire area of the wafer 101.

Figure 2:
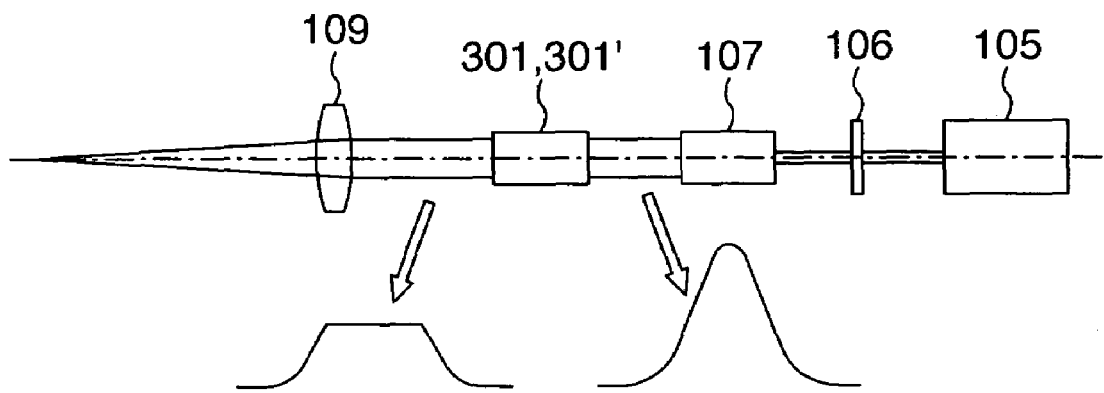
FIG. 2 is a diagram showing an example of the shaping of the beam by the beam shape optical system according to the invention.

The beam shape optical system 108 may be a diffraction optical element (DOE) 301' or homogenizer 301 (see FIG. 2). A homogenizer using an aspheric lens can be used as described in, for example, U.S. Pat. No. 6,295,168.

Figure 3:
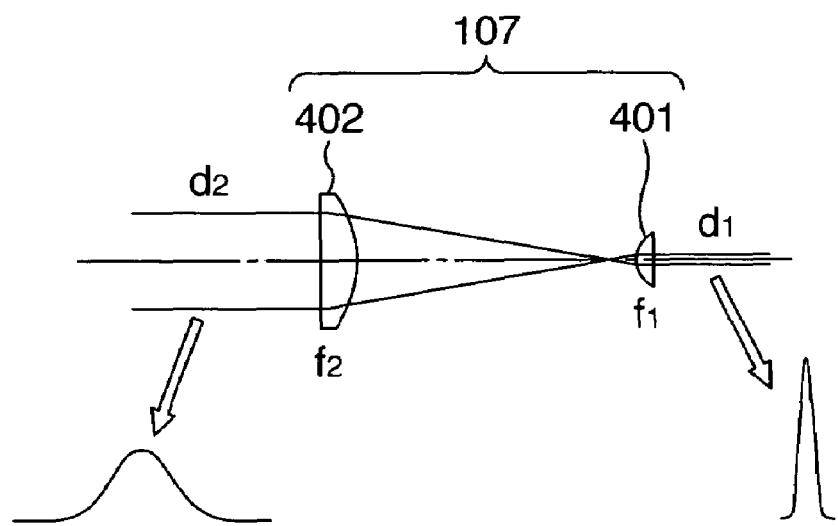
FIG. 3 is a diagram showing an example of the beam expander according to the invention.

The beam expander 107 to be used in the illumination optical system 103a is formed of plane-convex lenses 401 and 402 as shown in FIG. 3. If f1, f2, d1 and d2 respectively represent the focal length of the plane-convex lens 401, the focal length of the plane-convex lens 402, the diameter of the outgoing beam from the laser source 105 and the diameter of the outgoing beam from the beam expander 107, then an expression of d2=d1*f2/f1 can be satisfied.

Figure 4:
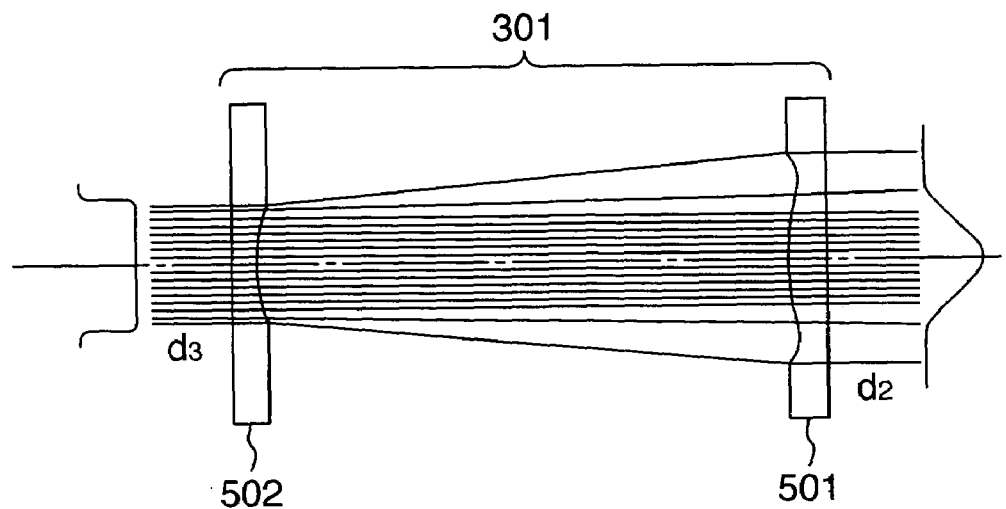
FIG. 4 is a diagram showing an example of the beam shape optical system as the homogenizer according to the invention.

FIGS. 2 and 4 show examples of the beam shape optical system using the homogenizer 301. The homogenizer 301 is composed of two aspheric lenses 501 and 502 as shown in FIG. 4. The aspheric lens 501 has such an aspheric surface as to change the Gauss distribution to a uniform intensity distribution on a plane. The aspheric surface shape of each aspheric lens is determined to estimate by using a computer. Thus, by the shape optical system 108 that uses the homogenizer 301 formed of two aspheric lenses 501 and 502, and the beam expander 107, the laser beam of the Gauss distribution can be expanded to the beam diameter d2 and then shaped to the beam diameter d3 so that the Gauss distribution can be converted to a flat illumination intensity distribution. This flattened-intensity beam is focused by the condenser lens 109 so that the slit-shaped beam 120 can be irradiated to the detection area on the wafer 101.

Figure 9:
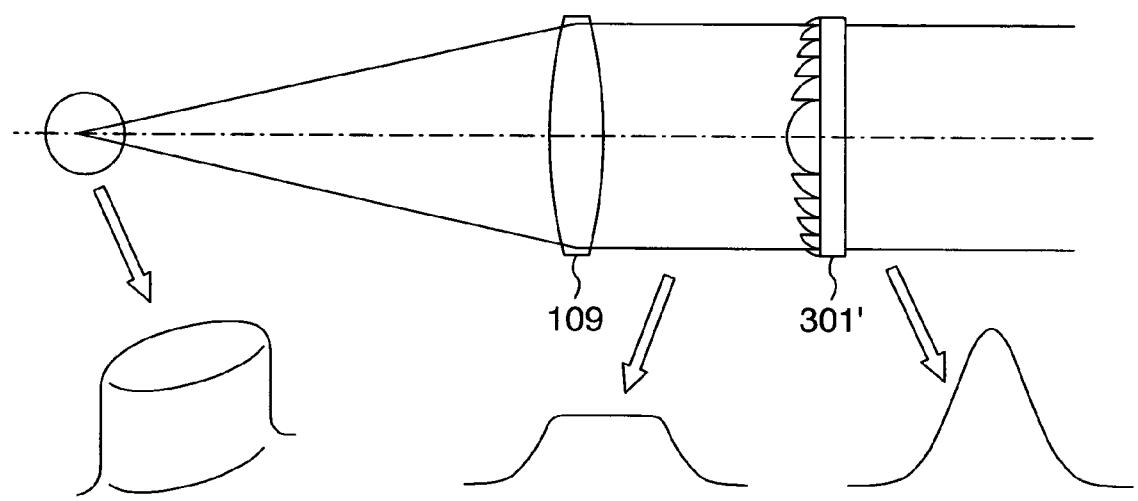
FIG. 9 is a diagram showing another example of the beam shape optical system using a diffraction optical element (DOE) according to the invention.

FIGS. 2 and 9 show examples of the beam shape optical system having the diffraction optical element (DOE) 301'. The Gauss distribution is shaped to be flat by the diffraction optical element (DOE) 301'. The flattened-distribution beam is focused and irradiated by the condenser lens 109 so as to illuminate the sample. The diffraction optical element (DOE) 301' is made of optical glass and has minute concavo-convex areas formed on its surface. The incident light to each of these minute areas is changed in its sense by the diffraction phenomena of light so that the Gauss distribution can be shaped into a flat distribution. These minute concavo-convex areas on the surface of the diffraction optical element (DOE) are produced by etching the glass surface after the optimum height, size and shape of each of these very small convex portions are determined by simulation.

Figure 10:
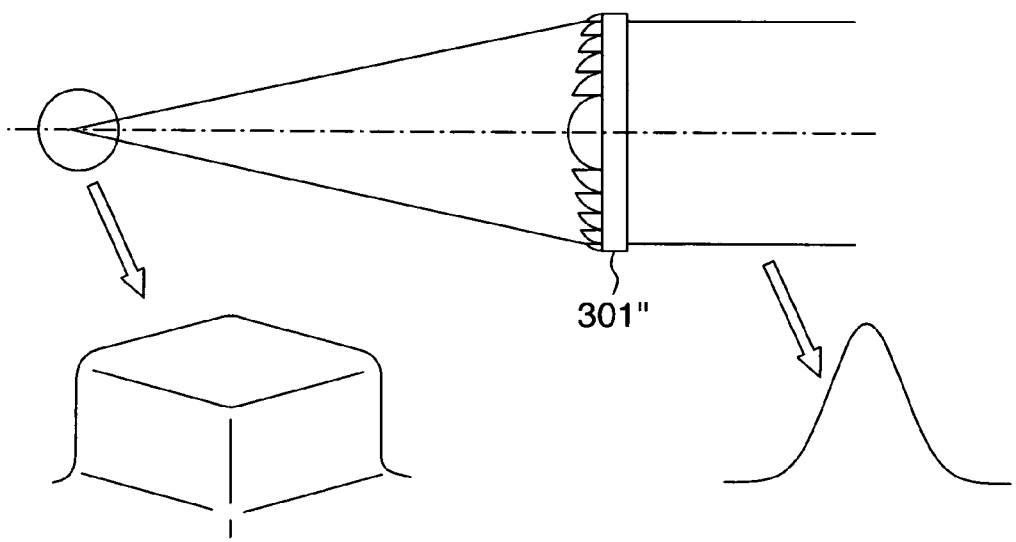
FIG. 10 is a diagram showing still another example of the beam shape optical system using the diffraction optical element (DOE) according to the invention.

FIG. 10 shows another example of the beam shape optical system using a diffraction optical element (DOE) 301". The characteristics of the diffraction optical element (DOE) 301" can be varied by changing the parameters of the above simulation. As illustrated in FIG. 10, the condenser lens 109 can be removed, and only the diffraction optical element (DOE) 301" is used to focus/irradiate the beam on the sample. By changing the parameters of the simulation, it is also possible to make the beam spot shape elliptical (or approximately elliptical) on the sample as in FIG. 9 or make it quadrangular (or approximately quadrangular) as in FIG. 10. When the beam spot shape is elliptical, the beam passing time of defect depends on how the defect passes within the illuminated area of the sample. On the contrary, when the beam spot shape is quadrangular, the defect passing time is constant, and thus this optical element is effective as illuminating means.

Figure 5:
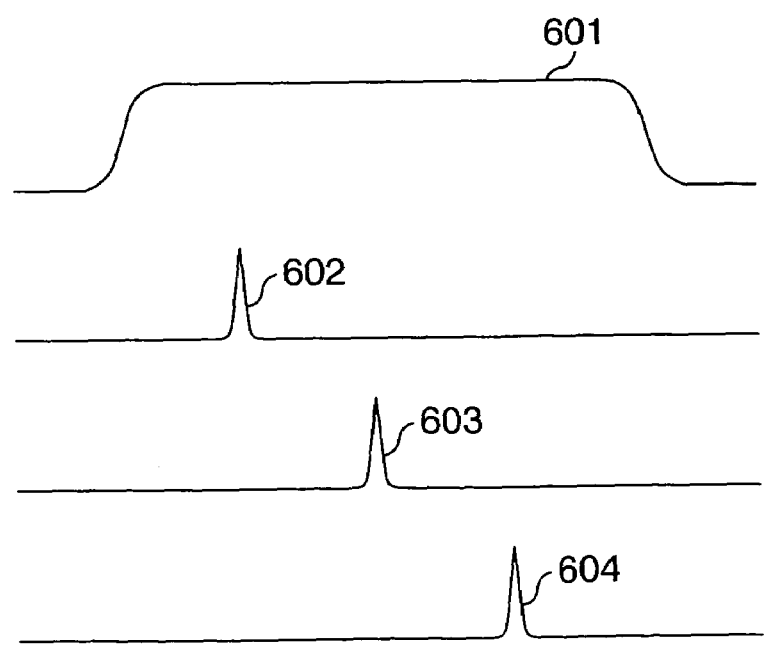
FIG. 5 is a diagram useful for explaining examples of detecting a foreign substance and defect by using a flattened beam shape according to the invention.

Thus, since the slit-shaped beam 120 has a flattened illumination intensity distribution 601 shown in FIG. 5, the scattered light from the same foreign substance and defect can be maintained substantially constant irrespective of their positions. Accordingly, the detected signals 602, 603 and 604 are substantially constant. Therefore, the detected signals from the same foreign substance and defect are always constant even after the same sample is repeatedly placed and set on the sample stage, or the reproducibility of the test can be improved.

Figure 6:
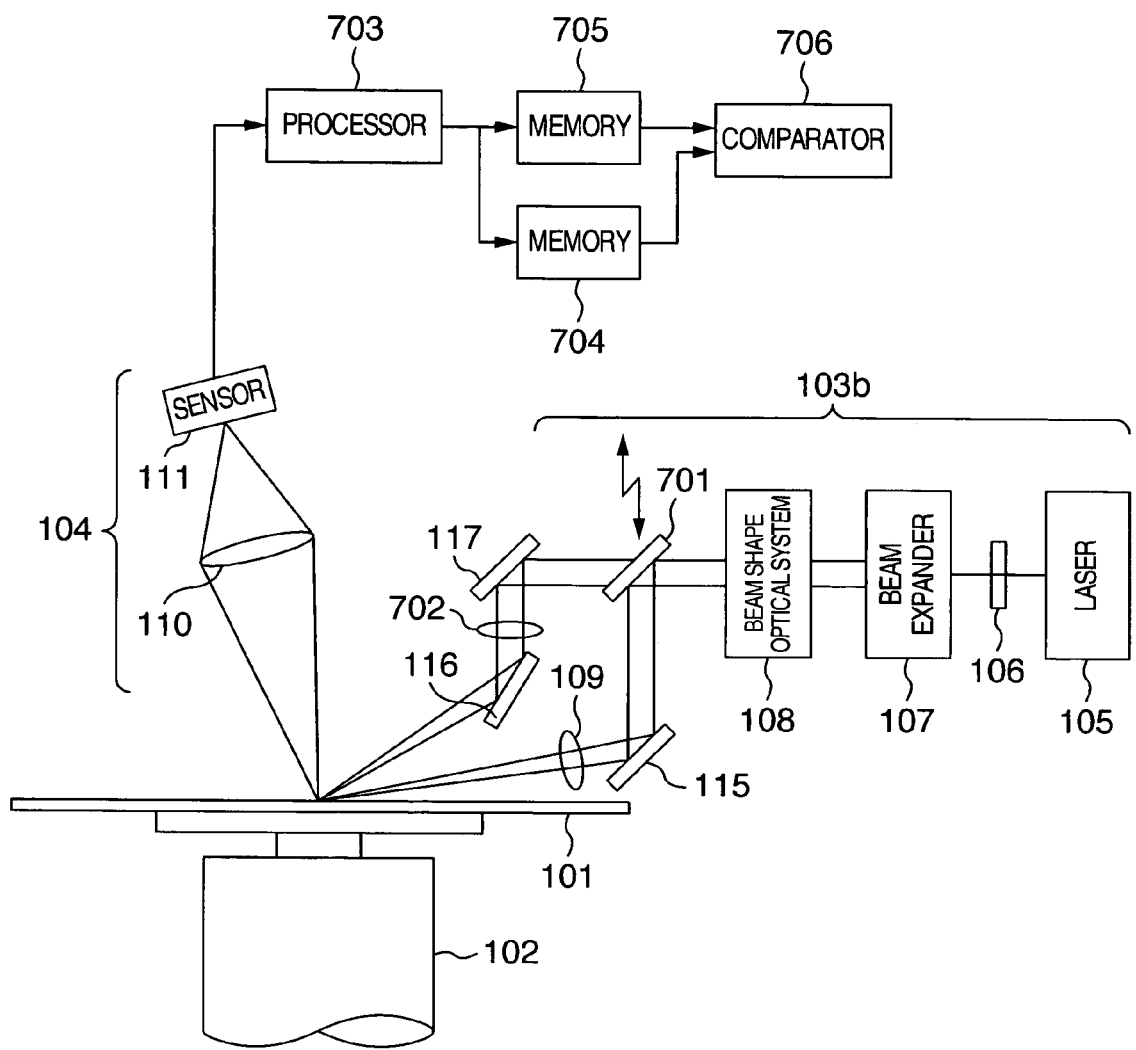
FIG. 6 is a diagram of a second embodiment of the defect detecting apparatus that is constructed so that a foreign substance and a defect on the semiconductor wafer can be separately detected according to the invention.

The second embodiment of the defect detecting apparatus according to the invention will be described with reference to FIG. 6. FIG. 6 is a diagram showing the construction of the second embodiment of the defect detecting apparatus according to the invention. The second embodiment is different from the first embodiment in that an illumination optical system 103b has a high-angle illumination optical system and a low-angle illumination optical system provided so that they can be switched. The scattered light in each illumination system is detected, and the detected signals in both systems are computed and compared so that the foreign substance and the defect (concavity and convexity) can be separately detected. In other words, in addition to the high-angle and low-angle illumination optical systems, the illumination optical system 103b has the common optical elements, namely, the laser source 105 that emits a laser beam having a Gauss distribution, the wavelength plate 106 for arbitrarily adjusting the polarization direction, the beam expander 107, and the shape optical system 108 for shaping the Gauss distribution into a flat illumination intensity distribution. The low-angle illumination optical system is formed of the mirror 115 and condenser lens 109, and the high-angle illumination optical system is composed of a mirror 117, a condenser lens 702 and a mirror 116. In addition, a movable mirror 701 is provided to switch both high-angle and low-angle systems. Thus, when the mirror 701 is in the optical axis, the, laser beam flattened (homogenized) in its illumination intensity distribution by the shape optical system 108 is passed through the low-angle illumination optical system. When the mirror 701 is out of the optical axis, the laser beam flattened (homogenized) in its illumination intensity distribution by the shape optical system 108 is passed through the high-angle illumination optical system. Thus, the sample is scanned over the entire surface by the low-angle beam having the homogenized intensity distribution. The scattered-light detected signal is subjected to necessary processes such as amplification and A/D conversion by a processor 703. Then, necessary information such as features of coordinates, luminance information (gradation information), the number of defects and area (size) are stored in a memory 704. Then, when the sample is scanned by the high-angle beam having the homogenized intensity distribution, the scattered-light detected signal is subjected to necessary processes such as amplification and A/D conversion by the processor 703. Thereafter, necessary information such as features of coordinates, luminance information (gradation information), the number of defects and area (size) are stored in a memory 705. After the completion of the test on the sample by the two different-angle beams, the contents of the memories 704 and 705, or the coordinates and luminance information stored in the memories 704 and 705 are used, and the luminance information of the foreign substance and defect at the same coordinates are compared and computed by a comparator 706 so that the foreign substance (convexity) and defect (concavity) can be separated. In other words, when the low-angle beam having the flattened (homogenized) intensity distribution is irradiated on the sample, the high-brightness scattered light (high-order diffracted light) can be obtained from a very small particle-shaped foreign substance (convex defect), if it is present. When the high-angle beam having the flattened (homogenized) intensity distribution is irradiated on the sample, the high-brightness scattered light (high-order diffracted light) can be obtained from a concave defect such as a scratch. Thus, by the comparison/computation at the same coordinates, it is possible to distinguish between the very small particle-shaped foreign substance and the minute scratch, or discriminate between the concave and convex defects.

Even if the memories 704 and 705 and the comparator 706 are replaced by a personal computer, the same effect can be obtained.

That is, since the scattered light intensity from a defect thus varies depending on its shape and on the illumination direction, the kind of the defect can be identified by comparing the intensities of the scattered light from the defect illuminated in different directions. If the defect is a convex-type defect such as a foreign substance adhered to the wafer, the scattered light intensity under low-angle illumination is greater than that under high-angle illumination. However, if the defect is a concave-type defect such as a scratch or COP (crystalline defect), the intensity of the scattered light produced under the low-angle illumination is contrarily less than that produced under the high-angle illumination. Thus, by taking a ratio between the scattered light intensities of both cases, it is possible to separate the convex-type and concave-type defects as shown in FIG. 11.

Figure 13:
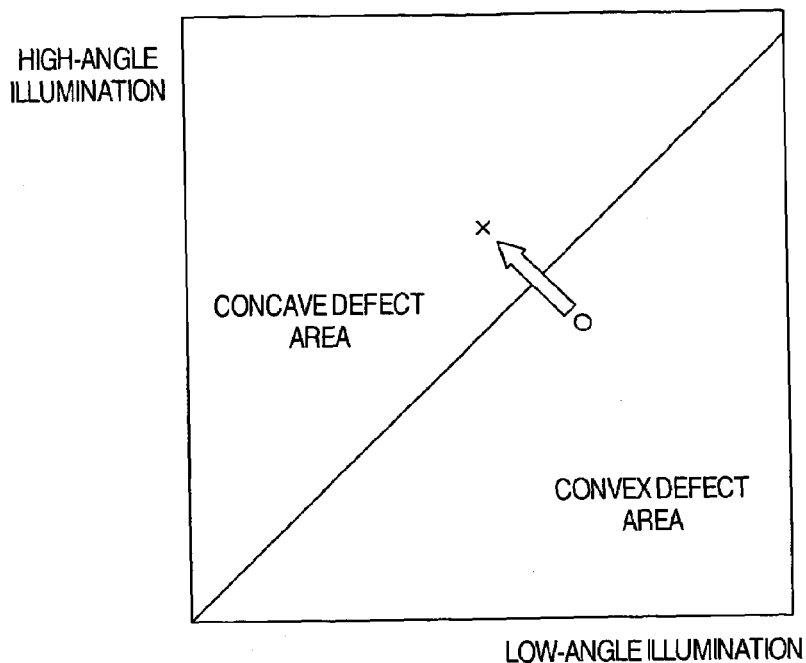
FIG. 13 is a diagram useful for explaining a comparative example in which the convex-type defect is misrecognized as the concave-type defect when the ratio is taken between the scattered light intensities obtained in the low-angle illumination and high-angle illumination.

Incidentally, the relative position of the defect to the illumination position is indefinite as described above. Therefore, when the illumination intensity distribution is a Gauss distribution, the relative position of the defect to the illumination intensity position varies each time the test is made as shown in FIGS. 12A and 12B, and the ratio between the scattered light intensities changes. The convex-type defect originally should show a relation of (scattered light intensity under low-angle illumination)>(scattered light intensity under high-angle illumination) as shown in FIG. 12A, but indicates the opposite relation of (scattered light intensity under high-angle illumination)>(scattered light intensity under low-angle illumination) of the concave-type defect as a result of the reverse of the ratio between the scattered light intensities as illustrated in FIG. 12B. That is, the classification of defect types becomes unstable as shown in FIG. 13.

However, according to the invention in which the illumination intensity distribution is flat, even if the relative position of the defect to the illumination position varies, the intensity of the scattered light produced from the defect becomes constant, and thus the defect types can be stably classified.

According to the second embodiment as described above, since the irradiated laser beam has a flattened (homogenized) intensity distribution of which the longitudinal dimension is in the range from a few tens of micrometers μm to several hundreds of μm, the detected signal from the same foreign substance and defect can be stably obtained even if the relative position of the defect and foreign substance to the laser beam irradiation position on the sample surface is changed each time the inspection is made after the switching of illumination angles. Thus, the foreign substance (convex-type defect) and the defect (concave-type defect) can be stably separated.

Figure 7:
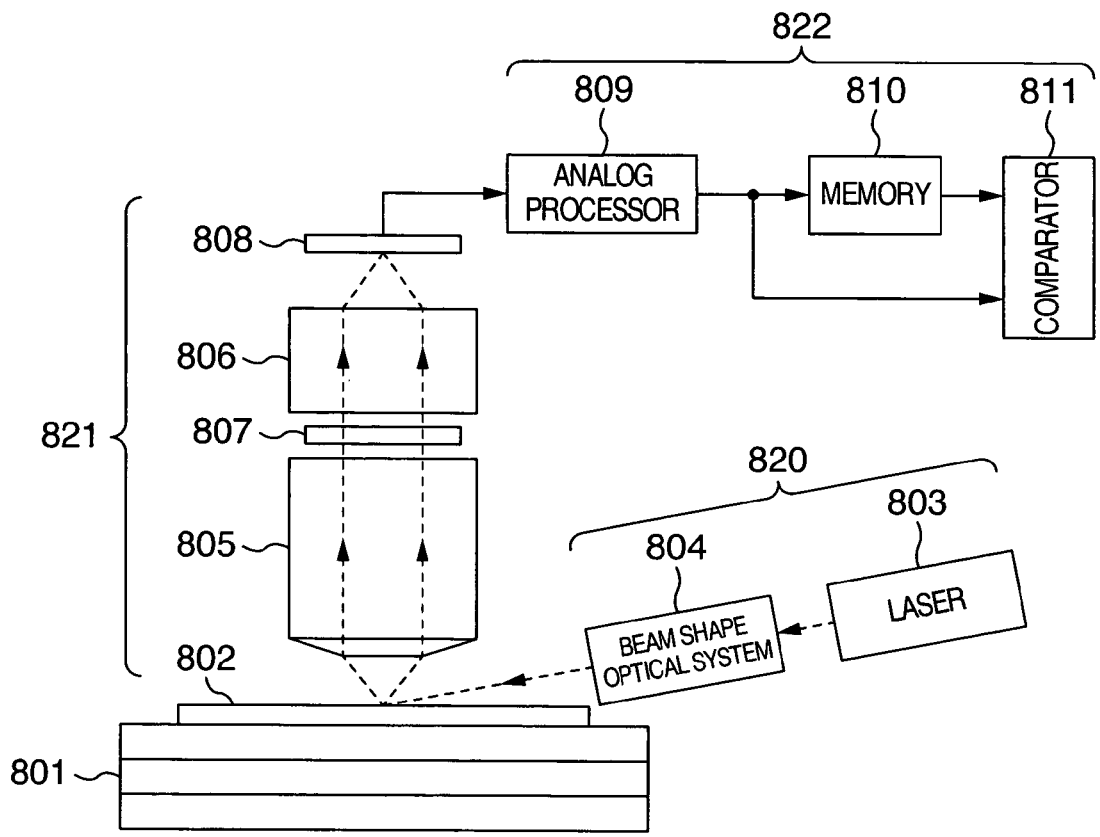
FIG. 7 is a diagram showing a third embodiment of the defect detecting apparatus that is constructed to detect a foreign substance and defect on the semiconductor wafer with circuit patterns formed thereon according to the invention.

The third embodiment of the defect detecting apparatus for detecting defects on semiconductor wafer according to the invention will be described with reference to FIG. 7. FIG. 7 shows the construction of the third embodiment of the defect detecting apparatus according to the invention. The beam shape optical system is useful even for the third embodiment that detects the defects on a wafer with circuit patterns formed thereon. The defect detecting apparatus of the third embodiment is composed of a wafer stage 801 that is movable in the X and Y directions together with a wafer 802 mounted thereon, an illumination optical system 820 for obliquely illuminating the wafer 802, a detection optical system 821 and a processor 822.

The illumination optical system 820 is formed of a laser source 803 and a beam shape optical system 804. The beam shape optical system 804 includes a necessary beam expander and condenser. The detection optical system 821 is comprised of a Fourier transform lens 805, an inverse Fourier transform lens 806, a spatial filter 807 and a sensor 808. The sensor 808 may be a TV camera, a linear sensor or TDI sensor. The processor 822 is composed of an analog processor 809, a memory 810 and a comparator 811. The diffracted light from the equi-pitch patterns on the wafer 802 is blocked off by the spatial filter 807, but the scattered light from the irregular-array patterns and foreign substance/defect passes through the spatial filter 807 and reaches the image sensor. The output from the image sensor 808 is amplified and converted from A (analog) to D (digital) by the analog processor 809. The memory 810 stores the information of just previous dice (coordinates, detected signal intensity and so on). The comparator 811 compares and computes this stored information and the current output from the analog processor 809 to remove the information of circuit patters and produce only the information of foreign substance and defects.

Figure 15:
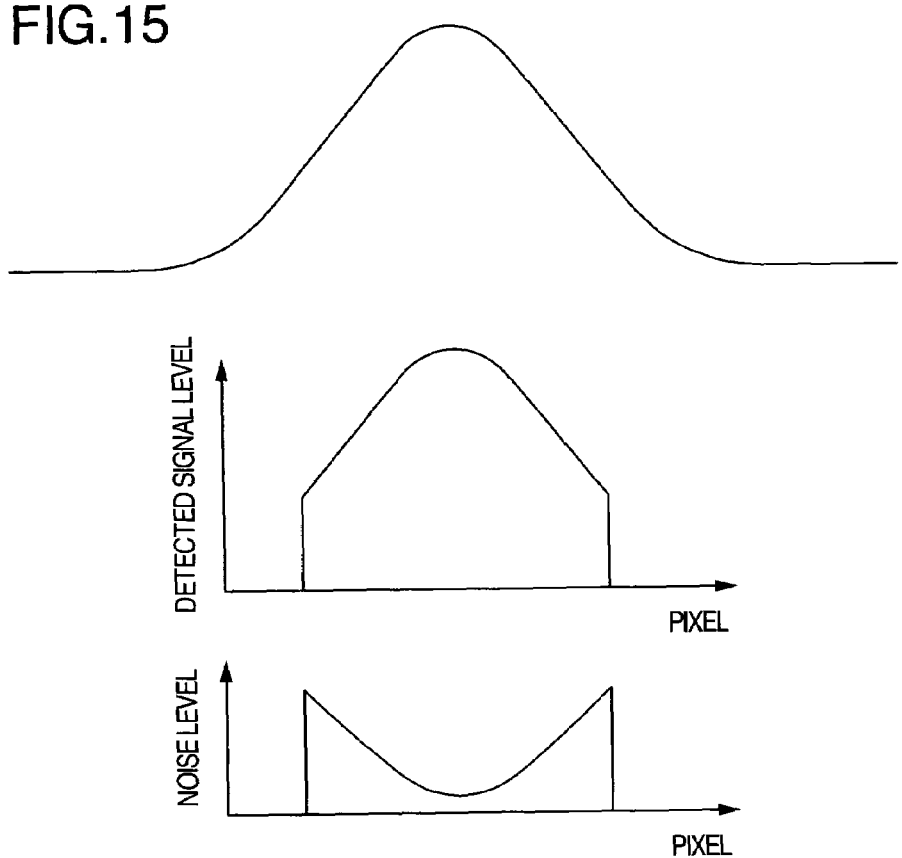
FIG. 15 is a diagram showing a comparative example of the signal and noise in the signal processing system when the illumination beam has a Gauss distribution.
Figure 16:
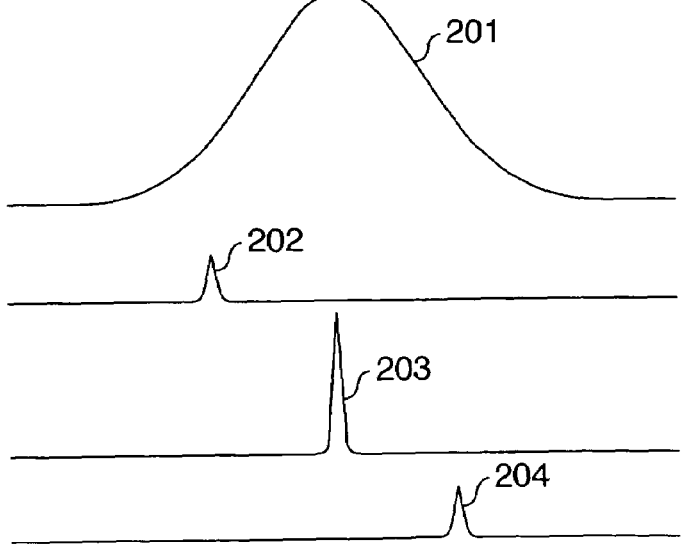
FIG. 16 is a diagram to which reference is made in explaining the prior art.

In this case, if the illumination by the laser beam has a Gauss distribution as shown in FIG. 15, a process called shading compensation is performed. When the illumination by the laser beam has a Gauss distribution, the level of the detected signal is proportional to the illumination intensity distribution and depends on each pixel, and thus the comparison/computation in the comparator 811 cannot be exactly performed. Therefore, the detected signal is amplified with the gain changed for each pixel so that the detected signal level from the same foreign substance/defect can be made equal. In this case, the higher the gain for pixels, the more noise those pixels generate.

Thus, in the third embodiment, the beam shape optical system 804 is used to make the detected signal level constant. Therefore, since the shading compensation is not necessary, the comparison/computation can be stably carried out.

Figure 8:
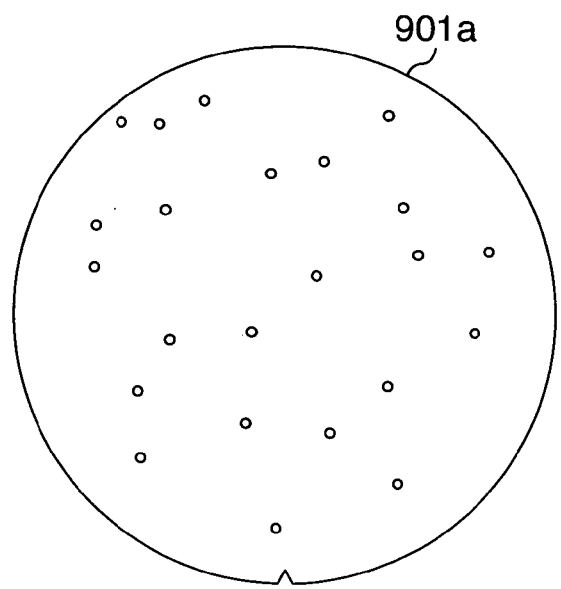
FIG. 8 is a diagram showing an example of the test result mapping according to the invention.
Figure 14A:
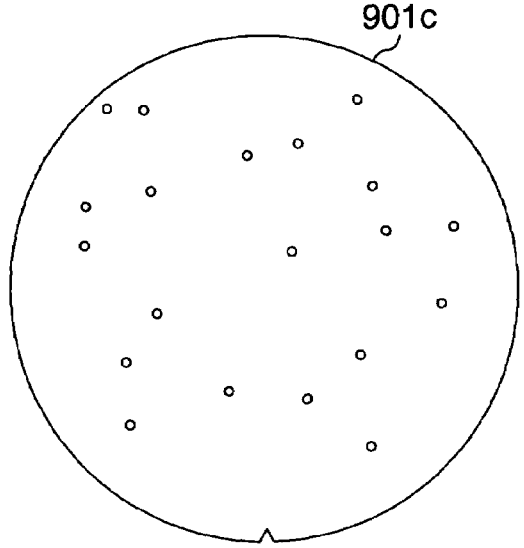
FIG. 14A is a diagram showing an example of the test result mapping when the illumination beam has a Gauss distribution.
Figure 14B:
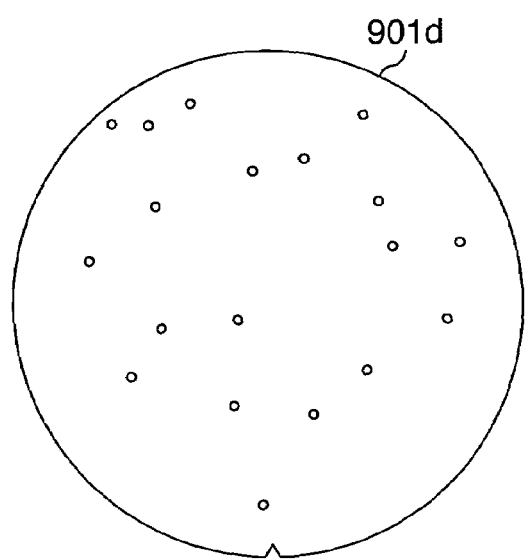
FIG. 14B is a diagram showing another example of the test result mapping when the illumination beam has a Gauss distribution.

According to the first through third embodiments mentioned above, since the foreign substance and defects can be stably detected, the result of the test shows that the mapping 901a can be stabilized as shown in FIG. 8 as compared to FIGS. 14A and 14B. The mapping information includes the positional information of foreign substance and defects, information of defect size and the number of defects. FIGS. 14A and 14B show the case of using the laser beam of a Gauss distribution for the illumination. Since foreign substance and defects are detected or not depending upon the Gauss distribution, the defect maps 901c and 901d are different from each other.

In addition, according to the first through third embodiment, since the flattened-distribution laser beam is used to illuminate, minute foreign substance and defects can be detected with stabilized sensitivity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims being therefore intended to be embraced therein.

The invention claimed is:

1. A defect detecting apparatus comprising:
a laser beam illumination optical system including:
a laser source for emitting a laser beam having a Gauss distribution in its illumination intensity,
a beam shape optical system for shaping said laser beam emitted from said laser source to be a laser beam having a flat distribution in its illumination intensity,
an optical path switching unit for switching an optical path of said distribution-flattened laser beam between a first optical path and a second optical path,
a high angle illuminator for illuminating said distribution-flattened laser beam switched to the first optical path by the optical path switching unit onto a substrate to be inspected, and
a low angle illuminator for illuminating said distribution-flattened laser beam switched to the second optical path by the optical path switching unit onto the substrate to be inspected;
a detection optical system that focuses and receives scattered light from said substrate on which said laser beam has been irradiated by said high angle illuminator and said low angle illuminator of said laser beam illumination optical system and that converts said received scattered light into a signal; and
a signal processor for detecting defects on said substrate and classifying the detected defects on the basis of said signal converted by said detection optical system from scattered light received by said high angle illuminator and said low angle illuminator.

2. A defect detecting apparatus according to claim 1, wherein said beam shape optical system of said laser beam illumination optical system is a diffraction optical element (DOE).

3. A defect detecting apparatus according to claim 1, wherein said beam shape optical system of said laser beam illumination optical system is a homogenizer.

4. A defect detecting apparatus according to claim 1, wherein said laser beam illumination optical system further has a beam expander provided between said beam shape optical system and said laser source in order to expand the beam diameter.

5. A defect detecting apparatus according to claim 1, wherein said laser beam illumination optical system is constructed to make high-angle illumination and low-angle illumination to said substrate by switching.

6. A defect detecting apparatus according to claim 5, wherein said signal processor is able to separately detect a minute foreign substance and a minute concavo-convex defect.

7. A defect detecting apparatus according to claim 1, wherein said detection optical system has a Fourier transform lens, an inverse Fourier transform, and a spatial filter provided in a common image surface between said Fourier transform lens and said inverse Fourier transform lens.

8. A defect detecting method comprising the steps of:
emitting from a laser source a laser beam having a Gauss distribution in its illumination intensity;
shaping said laser beam from said laser source to have a flat distribution in its illumination intensity;
switching an optical path of said shaped laser beam between a first optical path and a second optical path;
focusing and irradiating said shaped laser beam which is switched to the first optical path onto a substrate to be tested from a high angle;
focusing scattered light from said substrate as a result of said irradiation of said laser beam from a high angle;
receiving said focused scattered light caused by said irradiation from said high angle by a detector, and converting it by said detector into a first signal;
focusing and irradiating said shaped laser beam which is switched to a second optical path onto a substrate to be tested from a low angle;
focusing scattered light from said substrate as a result of said irradiation of the laser beam from said low angle;
receiving said focused scattered light caused by said irradiation from said low angle by a detector, and converting it by said detector into a second signal; and
processing said converted first signal and said converted second signal so as to detect defects on said substrate and classifying the detected defects on the basis of said converted first signal and said converted second signal.

9. A method according to claim 8, wherein a diffraction optical element (DOE) is used to shape said laser beam emitted from said laser source to have said flat distribution in its illumination intensity.

10. A method according to claim 8, wherein a homogenizer is used to shape said laser beam emitted from said laser source to have said flat distribution in its illumination intensity.

11. A method according to claim 10, wherein said laser beam is irradiated at either a high angle or a low angle by switching those angles, and scattered light from said substrate as a result of said irradiation is received and converted to a signal by a detector so that a minute foreign substance and a minute concavo-convex defect existing on said substrate can be separately detected.

12. A method according to claim 8, wherein said shaping of said laser beam to have said flat distribution is performed after expanding the beam diameter of said laser beam emitted from said laser source.

13. A method according to claim 8, wherein said laser beam shaped to have said flat distribution in its illumination intensity is irradiated at either a high angle or a low angle to said substrate by switching those angles.

14. A method according to claim 8, wherein scattered light obtained from said substrate as a result of said irradiation of said laser beam to said substrate is focused by a Fourier transform lens, part of said focused scattered light is blocked off by a spatial filter disposed in an image surface of said Fourier transform lens, and the light passed through said spatial filter is passed through an inverse Fourier transform lens to form an image on the acceptance surface of said detector so that said image can be detected.

15. A method according to claim 8, wherein said laser beam shaped to have said flat distribution in its illumination intensity and focused is further shaped to have a shape that is long in one direction, and then irradiated onto said substrate.

* * * * *